(12) United States Patent
Strong et al.

(10) Patent No.: US 8,239,978 B2
(45) Date of Patent: *Aug. 14, 2012

(54) VISION THROUGH PHOTODYNAMIC THERAPY OF THE EYE

(75) Inventors: H. Andrew Strong, North Vancouver (CA); Julia G. Levy, Vancouver (CA); Gustav Huber, Zurich (CH); Mario Fsadni, Buelach (CH)

(73) Assignee: Novartis Opthalmics AG, Basel (CH)

( * ) Notice: Subject to any disclaimer, the term of this patent is extended or adjusted under 35 U.S.C. 154(b) by 617 days.

This patent is subject to a terminal disclaimer.

(21) Appl. No.: 11/852,965

(22) Filed: Sep. 10, 2007

(65) Prior Publication Data

US 2008/0058403 A1 Mar. 6, 2008

Related U.S. Application Data

(63) Continuation of application No. 10/383,820, filed on Mar. 7, 2003, now abandoned, which is a continuation of application No. 09/300,979, filed on Apr. 28, 1999, now Pat. No. 6,548,542, which is a continuation of application No. 09/083,480, filed on May 22, 1998, now Pat. No. 5,910,510, which is a continuation of application No. 08/613,420, filed on Mar. 11, 1996, now Pat. No. 5,756,541.

(51) Int. Cl.
*A61K 31/295* (2006.01)

(52) U.S. Cl. ............................................ 4/502; 514/912

(58) Field of Classification Search .................. 514/502, 514/912
See application file for complete search history.

(56) References Cited

U.S. PATENT DOCUMENTS 5,633,275 A 5/1997 Mori et al.

FOREIGN PATENT DOCUMENTS

| HU | P9403385 | 2/1995 |
|---|---|---|
| JP | 02961074 | 10/1999 |
| WO | WO-93/00087 | 1/1993 |
| WO | WO-93/24127 | 12/1993 |
| WO | WO-95/24930 | 9/1995 |

OTHER PUBLICATIONS

Journal of Clinical Laser Medicine & Surgery (1997) 15(1):48.
Bunse et al., IOVS (1996) 37(3):S223.
Coffey et al., Lasers in Surgery and Medicine (1983) 3(2):167.
Haimovici et al., IOVS (1993) 34:1303 (Abstract No. 2955).
Lin et al., IOVS (1993) 34:1303 (Abstract No. 2953).
Miller et al., Archives of Ophthamology (1995) 113(6):810-818.
Miller et al., Chemical Abstracts (1995) 124:24930.
Mouton et al., IOVS (1993) 34:1169 (Abstract No. 2294).
Office Action for European Application No. 97 903 181.2, date mailed on Dec. 19, 2001, 5 pages.
Roberts et al., Photochemistry and Photobiology (1989) 49(Suppl):115S.
Schey et al., Database Biosis Online, Accession No. PREV200000426134 (2000).
Schey et al., Photochemistry and Photobiology (2000) 72(2):9 (Abstract only).
Schmidt et al., IOVS (1992) 33:1253 (Abstract No. 2802).
Schmidt-Erfuth et al., IOVS (1993) 34:1303 (Abstract No. 2956).
Schmidt-Erfuth et al., IOVS (1996) 37(3):580.
Walsh et al., IOVS (1993) 34:1303 (Abstract No. 2954).
Young et al., Archives of Ophthamology (1996) 114(2):186-192.
Rosenthal et al., Annals of Medicine (1994) 26:405-409.
Kukielczak et al., Current Topics in Biophysics (1995) 19(2):66-70.
Submissions of Publications from Japanese Patent Application No. 2006-064119, dated Apr. 16, 2010.
Trial Decision for Japanese Patent Application No. 9-532132, dated Jun. 9, 2008, 6 pages.

*Primary Examiner* — Zohreh Fay
(74) *Attorney, Agent, or Firm* — Morrison & Foerster LLP

(57) ABSTRACT

Photodynamic therapy of conditions of the eye, especially those conditions characterized by unwanted neovasculature, such as age-related macular degeneration, results in enhanced visual acuity for treated subjects.

24 Claims, 3 Drawing Sheets

VISUAL ACUITY
RETREATMENTS AT 2 AND 6 WEEKS
SNELLEN EQUIVALENT (LINES CHANGED FROM BASELINE)

| Patient No. | Baseline | T1W1 | T1W2 | T1W3 | T2W1 | T2W2 | T2W4 | T3W1 | T3W4 |
|---|---|---|---|---|---|---|---|---|---|
| 901 | 20/126 | | 20/80 (+2) | | | 20/40 (+5) | 20/40 (+5) | 20/40 (+5) | 20/40 (+5) |
| 902 | 20/250 | | 20/400 (-2) | | | 20/100 (+4) | | 20/80 (+5) | 20/160 (+2) |
| 903 | 20/80 | | 20/80 (0) | | | 20/32 (+3) | 20/25 (+4) | 20/50 (+2) | 20/40 (+3) |
| 904 | 20/640 | 20/400 (+2) | 20/250 (+4) | | | 20/320 (+3) | 20/320 (+3) | 20/320 (+2) | 20/250 (+4) |
| 905 | 20/320 | 20/250 (+1) | | 20/250 (+1) | 20/250 (+1) | | 20/250 (+1) | 20/200 (+2) | 20/160 (+3) |
| 906 | 20/200 | | 20/126 (+2) | | 20/100 (+3) | | | 20/100 (+3) | |
| 907 | 20/200 | 20/126 (+2) | | | 20/100 (+3) | | | | |
| 908 | 20/200 | 20/126 (+2) | | | 20/50 (+4) | | | | |
| 909 | 20/320 | 20/160 (+3) | | | 20/160 (+3) | | | | |
| 910 | 20/100 | 20/100 (0) | | | 20/126 (-1) | | | | |

T = PDT TREATMENT #
W = WEEKS AFTER TREATMENT

FIG. 3

VISION THROUGH PHOTODYNAMIC THERAPY OF THE EYE

CROSS-REFERENCE TO RELATED APPLICATIONS

This application is a continuation of U.S. application Ser. No. 10/383,820, filed Mar. 7, 2003, which is a continuation of U.S. application Ser. No. 09/300,979, filed Apr. 28, 1999, now U.S. Pat. No. 6,548,542, which is a continuation of U.S. application Ser. No. 09/083,480, filed May 22, 1998, now U.S. Pat. No. 5,910,510, which is a continuation of U.S. application Ser. No. 08/613,420, filed Mar. 11, 1996, now U.S. Pat. No. 5,756,541. The contents of each of these documents are incorporated herein by reference in their entirety.

TECHNICAL FIELD

The invention relates to a method to improve visual acuity by administering photodynamic therapy (PDT) to the eye.

BACKGROUND ART

Loss of visual acuity is a common problem associated with aging and with various conditions of the eye. Particularly troublesome is the development of unwanted neovascularization in the cornea, retina or choroid. Choroidal neovascularization leads to hemorrhage and fibrosis, with resultant visual loss in a number of recognized eye diseases, including macular degeneration, ocular histoplasmosis syndrome, myopia, and inflammatory diseases. Age-related macular degeneration (AMD) is the leading cause of new blindness in the elderly, and choroidal neovascularization is responsible for 80% of the severe visual loss in patients with this disease. Although the natural history of the disease is eventual quiescence and regression of the neovascularization process, this usually occurs at the cost of sub-retinal fibrosis and vision loss.

Current treatment of AMD relies on occlusion of the blood vessels using laser photocoagulation. However, such treatment requires thermal destruction of the neovascular tissue, and is accompanied by full-thickness retinal damage, as well as damage to medium and large choroidal vessels. Further, the subject is left with an atrophic scar and visual scotoma. Moreover, recurrences are common, and visual prognosis is poor.

Developing strategies have sought more selective closure of the blood vessels to preserve the overlying neurosensory retina. One such strategy is photodynamic therapy, which relies on low intensity light exposure of photosensitized tissues to produce deleterious effects. Photoactive compounds are administered and allowed to reach a particular undesired tissue which is then irradiated with a light absorbed by the photoactive compound. This results in destruction or impairment of the surrounding tissue.

Photodynamic therapy of conditions in the eye has been attempted over the past several decades using various photoactive compounds, e.g., porphyrin derivatives, such as hematoporphyrin derivative and Photofrin porfimer sodium; "green porphyrins", such as benzoporphyrin derivative (BPD), MA; and phthalocyanines. Schmidt, U. et al. described experiments using BPD coupled with low density lipoprotein (LDL) for the treatment of Greene melanoma (a nonpigmented tumor) implanted into rabbit eyes and achieved necrosis in this context (*IOVS* (1992) 33:1253 Abstract 2802). This abstract also describes the success of LDL-BPD in achieving thrombosis in a corneal neovascularization model. The corneal tissue is distinct from that of the retina and choroid.

Treatment of choroidal neovascularization using LDL-BPD or liposomal BPD has been reported in *IOVS* (1993) 34:1303: Schmidt-Erfurth, U. et al. (abstract 2956); Haimovici, R. et al. (abstract 2955); Walsh, A. W. et al. (abstract 2954). Lin, S. C. et al. (abstract 2953). An additional publication is Moulton, R. S. et al. (abstract 2294), *IOVS* (1993) 34:1169.

It has now been found that photodynamic treatment of eye conditions unexpectedly enhances the visual acuity of the subject.

DISCLOSURE OF THE INVENTION

The invention is directed to a method to improve visual acuity using photodynamic treatment methods. The methods are particularly effective when the photodynamic therapeutic protocol results in a diminution of unwanted neovasculature, especially neovasculature of the choroid.

Accordingly, in one aspect, the invention is directed to a method to enhance visual acuity which comprises administering to a subject in need of such treatment an amount of a formulation of a photoactive compound sufficient to permit an effective amount to localize in the eye of said subject; permitting sufficient time to elapse to allow an effective amount of said photoactive compound to localize in said eye; and irradiating the eye with light absorbed by the photoactive compound

BRIEF DESCRIPTION OF THE DRAWINGS

FIG. 3 shows the effect of repeated PDT in individual patients on maintaining enhanced visual acuity.

MODES OF CARRYING OUT THE INVENTION

In the general approach that forms the subject matter of the invention, a human subject whose visual acuity is in need of improvement is administered a suitable photoactive compound in amount sufficient to provide an effective concentration of the photoactive compound in the eye. After a suitable time period to permit an effective concentration of the compound to accumulate in the desired region of the eye, this region is irradiated with light absorbed by the photoactive compound. The irradiation results in excitation of the compound which, in turn, effects deleterious effects on the immediately surrounding tissue. The ultimate result is an enhancement of visual acuity in the subject.

Photoactive Compounds

The photodynamic therapy according to the invention can be performed using any of a number of photoactive compounds. For example, various derivatives of hematoporphyrin have been described, including improvements on hematoporphyrin derivative per se such as those described in U.S. Pat. Nos. 5,028,621; 4,866,168; 4,649,151; and 5,438,071, the entire contents of which are incorporated herein by reference. In addition, pheophorbides are described in U.S. Pat. Nos. 5,198,460; 5,002,962; and 5,093,349; bacteriochlorins in U.S. Pat. Nos. 5,171,741 and 5,173,504; dimers and trimers of hematoporphyrins in U.S. Pat. Nos. 4,968,715 and 5,190, 966. The contents of these patents are also incorporated herein by reference. In addition, U.S. Pat. No. 5,079,262 describes the use of a precursor to hematoporphyrin, aminolevulinic acid (ALA), as the source of a photoactive compound. The use of phthalocyanine photosensitizers in photodynamic therapy is described in U.S. Pat. No. 5,166,197. The contents of all of the foregoing patents are incorporated herein by reference. Other possible photoactive compounds include purpurins, merocyanines and porphycenes. Particular preferred photoactive compounds for use in the invention method are the green porphyrins. These porphyrins are described in U.S. Pat. Nos. 4,883,790; 4,920,143; 5,095,030; and 5,171,749, the entire contents of which are incorporated herein by reference. As these photoactive agents represent a particularly preferred embodiment, typical formulas for these compounds are represented herein in FIG. 1.

Referring to FIG. 1, in preferred embodiments each of $R^1$ and $R^2$ is independently selected from the group consisting of carbalkoxyl (2-6C), alkyl (1-6C), arylsulfonyl (6-10C), cyano and —$CONR^5CO$ wherein $R^5$ is aryl (6-10C) or alkyl (1-6C); each $R^3$ is independently carboxyl, carboxyalkyl (2-6C) or a salt, amide, ester or acylhydrazone thereof or is alkyl (1-6C); $R^4$ is CH=$CH_2$ or —CH($OR^{4'}$)CH3 wherein $R^{4'}$ is H, or alkyl (1-6C) optionally substituted with a hydrophilic substituent. Especially preferred also are green porphyrins of the formula shown in FIGS. 1C or 1D or mixtures thereof.

Figure 1A:
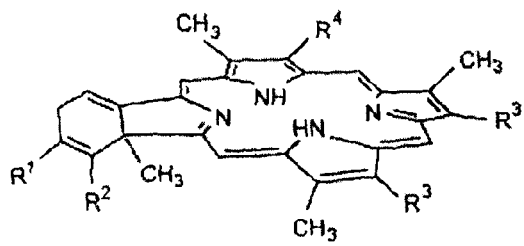
FIGS. 1A-1F show preferred forms of the green porphyrins useful in the methods of the invention.
Figure 1B:
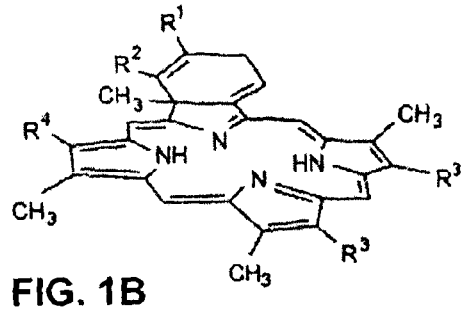
Figure 1C:
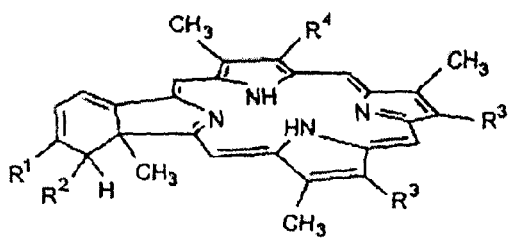
Figure 1D:
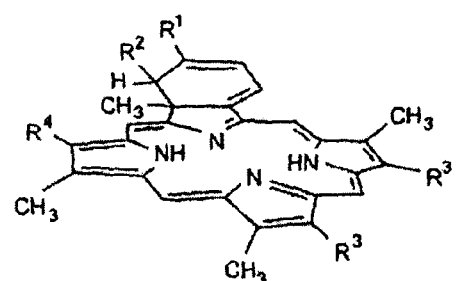
Figure 1E:
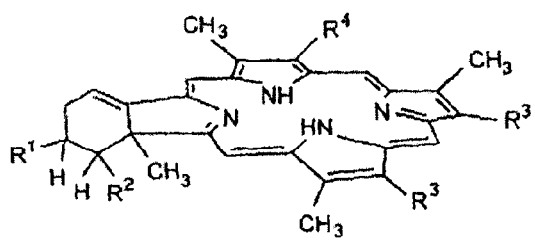
Figure 1F:
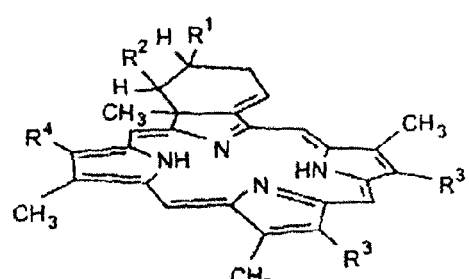

More preferred are embodiments are those wherein the green porphyrin is of the formula shown in FIG. 1C or 1D or a mixture thereof and wherein each of $R^1$ and $R^2$ is independently carbalkoxyl (2-6C); one $R^3$ is carboxyalkyl (2-6C) and the other $R^3$ is an ester of a carboxyalkyl (2-6C) substituent; and $R^4$ is CH=$CH_2$ or —CH(OH)$CH_3$.

Still more preferred are embodiments wherein green porphyrin is of the formula shown in FIG. 1C and wherein $R^1$ and $R^2$ are methoxycarbonyl; one $R^3$ is —$CH_2CH_2COOCH_3$ and the other $R^3$ is $CH_2CH_2COOH$; and $R^4$ is CH=$CH_2$; i.e., BPD-MA.

Any of the photoactive compounds described above can be used in the method of the invention; of course, mixtures of two or more photoactive compounds can also be used; however, the effectiveness of the treatment depends on the absorption of light by the photoactive compound so that if mixtures are used, components with similar absorption maxima are preferred.

Formulations

The photoactive agent is formulated so as to provide an effective concentration to the target ocular tissue. The photoactive agent may be coupled to a specific binding ligand which may bind to a specific surface component of the target ocular tissue or, if desired, by formulation with a carrier that delivers higher concentrations to the target tissue.

The nature of the formulation will depend in part on the mode of administration and on the nature of the photoactive agent selected. Any pharmaceutically acceptable excipient, or combination thereof, appropriate to the particular photoactive compound may be used. Thus, the photoactive compound may be administered as an aqueous composition, as a transmucosal or transdermal composition, or in an oral formulation. The formulation may also include liposomes. Liposomal compositions are particularly preferred especially where the photoactive agent is a green porphyrin. Liposomal formulations are believed to deliver the green porphyrin selectively to the low-density lipoprotein component of plasma which, in turn acts as a carrier to deliver the active ingredient more effectively to the desired site. Increased numbers of LDL receptors have been shown to be associated with neovascularization, and by increasing the partitioning of the green porphyrin into the lipoprotein phase of the blood, it appears to be delivered more efficiently to neovasculature.

As previously mentioned, the method of the invention is particularly effective where the loss of visual acuity in the patient is associated with unwanted neovasculature. Green porphyrins, and in particular BPD-MA, strongly interact with such lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins involving lipocomplexes, including liposomes, are described in U.S. Pat. No. 5,214,036 and in U.S. Ser. No. 07/832,542 filed 5 Feb. 1992, the disclosures of both of these being incorporated herein by reference. Liposomal BPD-MA for intravenous administration can also be obtained from QLT PhotoTherapeutics Inc., Vancouver, British Columbia.

Administration and Dosage

The photoactive compound can be administered in any of a wide variety of ways, for example, orally, parenterally, or rectally, or the compound may be placed directly in the eye. Parenteral administration, such as intravenous, intramuscular, or subcutaneous, is preferred. Intravenous injection is especially preferred.

The dose of photoactive compound can vary widely depending on the mode of administration; the formulation in which it is carried, such as in the form of liposomes; or whether it is coupled to a target-specific ligand, such as an antibody or an immunologically active fragment. As is generally recognized, there is a nexus between the type of photoactive agent, the formulation, the mode of administration, and the dosage level. Adjustment of these parameters to fit a particular combination is possible.

While various photoactive compounds require different dosage ranges, if green porphyrins are used, a typical dosage is of the range of 0.1-50 mg/$M^2$ (of body surface area) preferably from about 1-10 mg/$M^2$ and even more preferably about 2-8 mg/$M^2$.

The various parameters used for effective, selective photodynamic therapy in the invention are interrelated. Therefore, the dose should also be adjusted with respect to other parameters, for example, fluence, irradiance, duration of the light used in photodynamic therapy, and time interval between administration of the dose and the therapeutic irradiation. All of these parameters should be adjusted to produce significant enhancement of visual acuity without significant damage to the eye tissue.

Stated in alternative terms, as the photoactive compound dose is reduced, the fluence required to close choroidal neovascular tissue tends to increase.

Light Treatment

After the photoactive compound has been administered, the target ocular tissue is irradiated at the wavelength absorbed by the agent selected. The spectra for the photoactive compounds described above are known in the art; for any particular photoactive compound, it is a trivial matter to ascertain the spectrum. For green porphyrins, however, the desired wavelength range is generally between about 550 and 695 nm. A wavelength in this range is especially preferred for enhanced penetration into bodily tissues.

As a result of being irradiated, the photoactive compound in its excited state is thought to interact with other compounds to form reactive intermediates, such as singlet oxygen, which can cause disruption of cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to endothelial cells, with subsequent platelet adhesion, degranulation, and thrombus formation.

The fluence during the irradiating treatment can vary widely, depending on type of tissue, depth of target tissue, and the amount of overlying fluid or blood, but preferably varies from about 50-200 Joules/cm$^2$.

The irradiance typically varies from about 150-900 mW/cm$^2$, with the range between about 150-600 mW/cm$^2$ being preferred. However, the use of higher irradiances may be selected as effective and having the advantage of shortening treatment times.

The optimum time following photoactive agent administration until light treatment can also vary widely depending on the mode of administration, the form of administration and the specific ocular tissue being targeted. Typical times after administration of the photoactive agent range from about 1 minute to about 2 hours, preferably bout 5-30 minutes, and more preferably 10-25 minutes.

The duration of light irradiation depends on the fluence desired; for an irradiance of 600 mW/cm$^2$ a fluence of 50 J/cm$^2$ requires 90 seconds of irradiation; 150 J/cm$^2$ requires 270 seconds of irradiation.

Evaluation of Treatment

Clinical examination and fundus photography typically reveal no color change immediately following photodynamic therapy, although a mild retinal whitening occurs in some cases after about 24 hours. Closure of choroidal neovascularization is preferably confirmed histologically by the observation of damage to endothelial cells. Observations to detect vacuolated cytoplasm and abnormal nuclei associated with disruption of neovascular tissue may also be evaluated.

In general, effects of the photodynamic therapy as regards reduction of neovascularization can be performed using standard fluorescein angiographic techniques at specified periods after treatment.

Of paramount importance with respect to the present invention is the evaluation of visual acuity. This is done using means standard in the art and conventional "eye charts" in which visual acuity is evaluated by the ability to discern letters of a certain size, usually with five letters on a line of given size. Measures of visual acuity are known in the art and standard means are used to evaluate visual acuity according to the present invention.

The following examples are to illustrate but not to limit the invention.

EXAMPLE 1

Comparison of Various PDT Regimens

Groups of patients who had been diagnosed as qualified for experimental treatment of age-related macular degeneration (AMD) were divided into three groups.

Group A, of 22 patients, was treated with a regimen in which they were administered 6 mg/M$^2$ (of body surface area) of BPD-MA in the commercially available liposomal intravenous composition obtainable from QLT PhotoTherapeutics, Vancouver, BC. Administration was intravenous. Thirty minutes after the start of infusion, these patients were administered irradiance of 600 mW/cm$^2$ and total fluence of either 50 J/cm$^2$, 75 J/cm$^2$, 100 J/cm$^2$, 105 J/cm$^2$ or 150 J/cm$^2$ of light from a coherent Argon dye laser No. 920, Coherent Medical Laser, Palo Alto, Calif. (Ohkuma, H. et al. *Arch Ophthalmol* (1983) 101:1102-1110; Ryan, S. J., *Arch Ophthalmol* (1982) 100:1804-1809).

A second group of 15 patients, Group B, was also administered 6 mg/M$^2$ BPD-MA in the liposomal formulation, intravenously as in Group A, but irradiation, conducted as described for Group A, began 20 minutes after the start of infusion.

The 15 patients in Group C were subjected to a regime identical to those in Group A except that the BPD-MA was administered at 12 mg/M$^2$ To evaluate the patients after treatment, fluorescein angiography was performed 1 week, 4 weeks and 12 weeks after treatment. Visual acuity tests using standard eye charts were administered 3 months after treatment. The change in visual acuity was averaged for each group regardless of the total fluence of light administered.

After 3 months, patients subjected to regimen A showed an improvement in visual acuity of +0.10 (an improvement of 1.0 would indicate an improvement of one line on the conventional eye charts). Patients subjected to regimen B showed an enhancement of visual acuity of +0.53; those on regimen C decreased in visual acuity at an average of −0.40.

By comparison, 184 patients treated using standard photocoagulation treatment as described by a Macular Photocoagulation Study Group in *Clinical Sciences* (1991) 109:1220-1231, showed a diminution in visual acuity 3 months after treatment of −3.0. This was worse than the results of no treatment where a sample of 179 patients suffering from AMD showed a loss of visual acuity over this time period of −2.0.

Thus, it appeared that regimen B wherein 6 mg/M$^2$ of BPD in a liposomal formulation were administered and irradiation began 20 minutes later was the best of these three protocols tested.

EXAMPLE 2

Time Course of Enhancement of Visual Acuity

Sixteen patients in the study were subjected to regimen B described in Example 1 above and evaluated for visual acuity after 1 week and after 4 weeks as well as after 3 months. One week after treatment these patients had an average increase in visual acuity of +2.13; 4 weeks after treatment the average was +1.25 and after 3 months, +0.53.

These results seemed at least partly to correlate with success in closing choroidal neovasculature (CNV). For those patients in regimen B, 10 of the 16 tested by fluorescein angiography showed CNV more than 50% closed after 4 weeks with a corresponding increase in visual acuity of +1.6. The remaining 6 patients who showed less than 50% closure of CNV after 4 weeks showed an enhanced visual acuity of +0.7.

Of 15 patients subjected to regimen C of Example 1, 7 showed more than 50% closure of CNV and an enhanced visual acuity of +1.4. Three of the 15 showed less than 50% closure of CNV and showed a loss of visual acuity of −0.3. Five of the 15 showed classic CNV recurrence and showed a loss of visual acuity of −1.6.

On the other hand, after 4 weeks of treatment with regimen A, 9 of 21 patients showed a CNV of more than 50% closure but a decline in visual acuity of −0.2. Nine of the 21 showed a closure of CNV of less than 50% and an enhanced visual acuity of +0.9. Three of the 21 patients treated who showed classic CNV recurrence showed no change in visual acuity.

After 3 months, the results are as shown in Table 1, where the change in visual acuity observed is noted.

TABLE 1

|  | Regimen A | Regimen B | Regimen C |
|---|---|---|---|
| Classic CNV ≧50% closed | +0.7 (3/20) | +3 (4/13) | — (0/12) |
| Classic CNV <50% closed | +0.14 (7/20) | 0 (3/13) | +1.75 (4/12) |
| Classic CNV Recurrence | −0.1 (10/20) | −0.3 (6/13) | −1.4 (8/12) |

Thus, there appears to be some, but far from perfect correlation between CNV closure and enhancement of visual acuity. The method of the invention may thus be most readily applied to patients showing unwanted neovasculature, especially in the choroid. Thus, suitable indications would include macular degeneration, ocular histoplasmosis syndrome, myopia, and inflammatory diseases.

Figure 2:
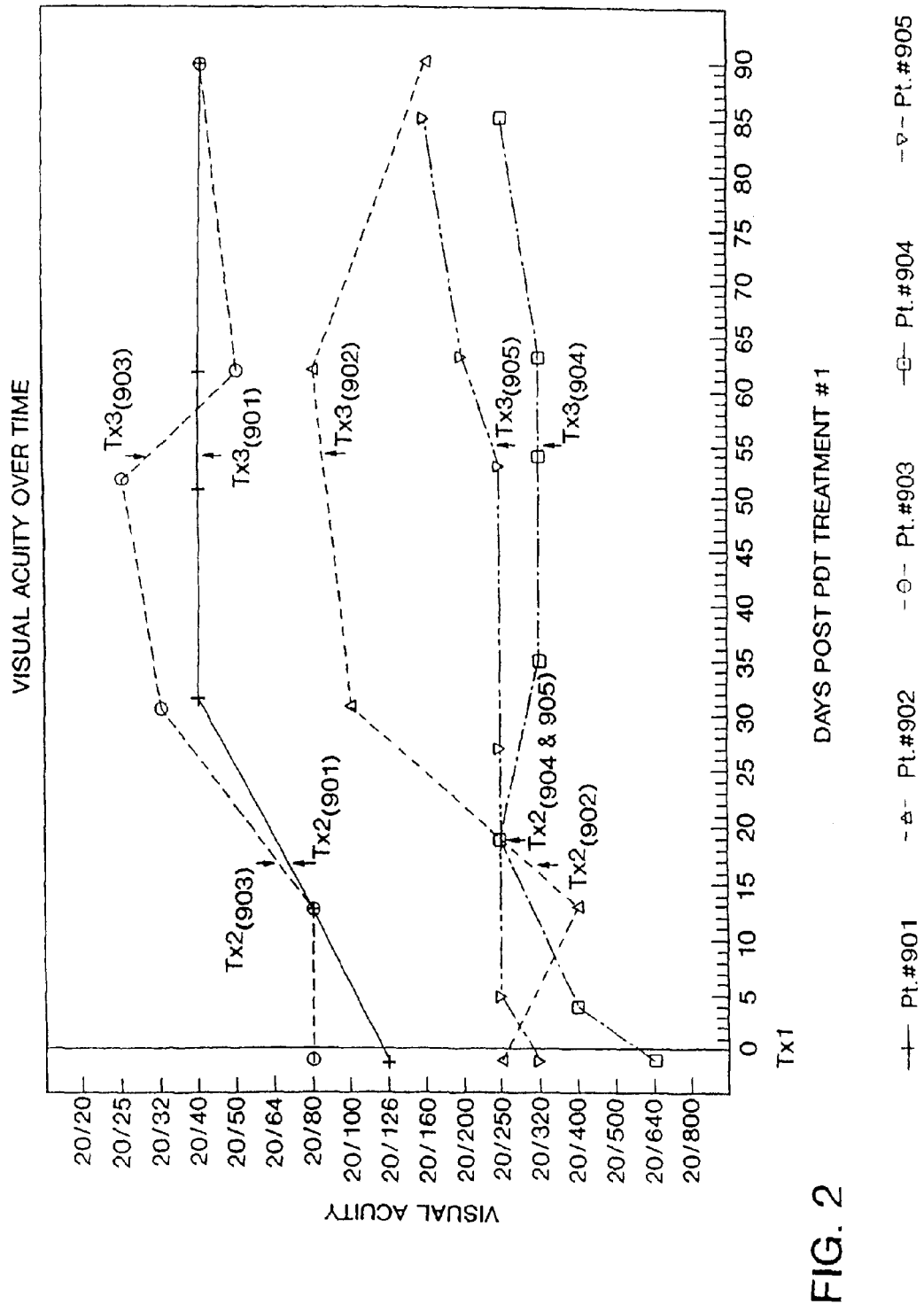
FIG. 2 shows the visual acuity response of individual patients subjected to PDT over time.

FIG. 2 shows a graphic representation of the time course of change in visual acuity of individual patients subjected to regimen B. All patients showed improvement, although in some cases the improvement diminished over time after treatment.

EXAMPLE 3

Effect of Iterative Treatment

Individual patients were treated with regimen B as described in Example 1 and then retreated at 2 and 6 weeks from the initial treatment. Repeating the treatment appeared to enhance the degree of increased visual acuity. The results are summarized in FIG. 3.

As shown in FIG. 3, for example, patient no. 901 starting at a base line of 20/126 showed an enhancement of +2 in visual acuity after week 2; two weeks after a second treatment, the enhancement was +5 over base line. For patient 906, the enhancement after the first treatment at week 2 was +2; this increased to +3 one week after a second treatment. While some patients showed slight relapses, in general, repeating the regimen maintained or increased enhancement of visual acuity.

The invention claimed is:

1. A method to enhance visual acuity as determined by ability to discern letters of certain sizes in standard eye charts in a human subject, which method comprises:
   (a) irradiating target ocular tissue in said subject with light absorbed by a photoactive compound that has been administered to said subject and localized to said ocular tissue, and
   (b) repeating said administering said photoactive compound and irradiating of ocular tissue at least once;
   whereby visual acuity in said subject is enhanced.

2. The method of claim 1 wherein an eye of said subject contains unwanted neovasculature.

3. The method of claim 2 wherein the neovasculature is choroidal neovasculature.

4. The method of claim 1 wherein the photoactive compound is a green porphyrin, a hematoporphyrin derivative, a chlorin, or a phlorin.

5. The method of claim 4 wherein the photoactive compound is a green porphyrin of the formula

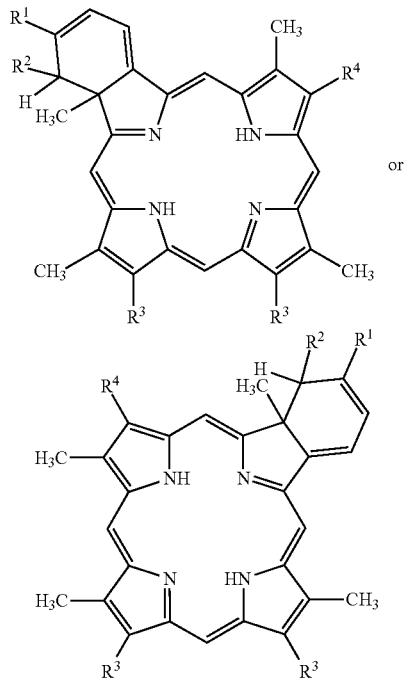

wherein each of $R^1$ and $R^2$ is independently selected from the group consisting of carbalkoxyl (2-6C), alkyl (1-6C), arylsulfonyl (6-10C), cyano and —$CONR^5CO$— wherein $R^5$ is aryl (6-10C) or alkyl (1-6C);

each $R^3$ is independently carboxyl, carboxyalkyl (2-6C) or a salt, amide, ester or acyl hydrazone thereof, or is alkyl (1-6C);

$R^4$ is CH=$CH_2$ or —CH(OR$^{4'}$)$CH_3$ wherein $R^{4'}$ is H, or alkyl (1-6C) optionally substituted with a hydrophilic substituent.

6. The method of claim 1 wherein said photoactive compound is contained in a liposomal preparation.

7. The method of claim 1 wherein said subject has been diagnosed with age-related macular degeneration (AMD).

8. The method of claim 1 wherein the subject has been diagnosed with a condition selected from the group consisting of macular degeneration, ocular histoplasmosis syndrome, myopia, and inflammatory diseases.

9. The method of claim 1 wherein said irradiation is administered at an irradiance of about 600 mW/cm$^2$ to provide a total fluence of 50 J/cm$^2$-150 J/cm$^2$ of said light.

10. The method of claim 1, wherein said repeating is performed two weeks following the irradiating of ocular tissue in step (a).

11. A method of detecting an improvement in visual acuity, said method comprising measuring visual acuity as determined by ability to discern letters of certain sizes in standard eye charts of a human subject, which method comprises:
   (a) irradiating target ocular tissue in said subject with light absorbed by a photoactive compound that has been administered to said subject and localized to said ocular tissue, and
   (b) repeating said administering said photoactive compound and irradiating of ocular tissue at least once; followed by
   (c) measuring visual acuity in said subject by determining ability to discern letters of certain sizes in standard eye charts, thereby detecting an improvement in visual acuity.

12. The method of claim 10, which further comprises (c) repeating said administering said photoactive compound and irradiating of ocular tissue at least once six weeks following the irradiating of ocular tissue in step (b).

13. The method of claim 1 wherein said irradiation is administered beginning about 5-30 minutes after said subject has been administered said photoactive compound.

14. The method of claim 4 wherein said green porphyrin is of the formula

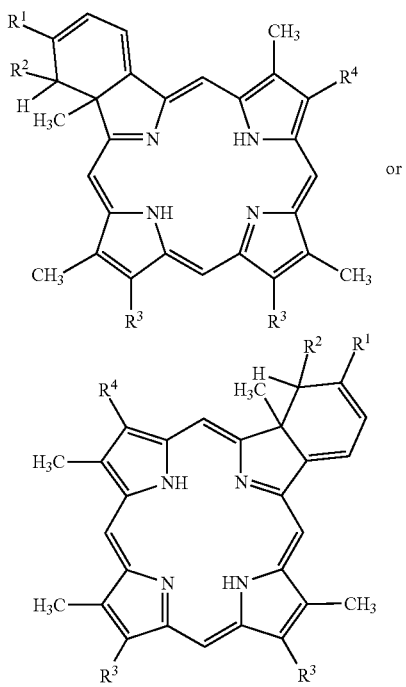

or wherein each of $R^1$ and $R^2$ is independently carbalkoxyl (2-6C);
one $R^3$ is carboxyalkyl (2-6C) and the other $R^3$ is the ester of a carboxyalkyl (2-6C) substituent; and
$R^4$ is CH=CH$_2$ or —CH(OH)CH$_3$.

15. The method of claim 14 wherein said green porphyrin is of the formula

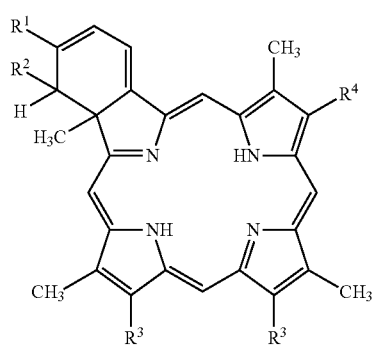

and
wherein $R^1$ and $R^2$ are methoxycarbonyl;
one $R^3$ is —CH$_2$CH$_2$COOCH$_3$ and the other $R^3$ is CH$_2$CH$_2$COOH; and
$R^4$ is CH=CH$_2$.

16. The method of claim 1 wherein said irradiation is administered beginning about 5 minutes after said subject has been administered said formulation.

17. The method of claim 1, wherein the light is emitted from a laser.

18. The method of claim 1, further comprising measuring visual acuity in the subject.

19. The method of claim 11 wherein the photoactive compound is a green porphyrin, a hematoporphyrin derivative, a chlorin, or a phlorin.

20. The method of claim 19 wherein said photoactive agent is a green porphyrin of the formula

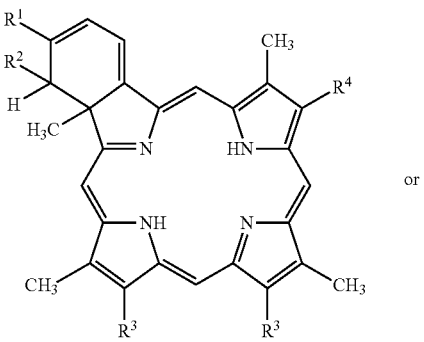

or

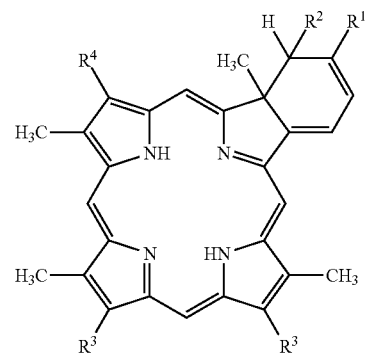

wherein each of $R^1$ and $R^2$ is independently selected from the group consisting of carbalkoxyl (2-6C), alkyl (1-6C), arylsulfonyl (6-10C), cyano and —CONR$^5$CO— wherein $R^5$ is aryl (6-10C) or alkyl (1-6C);
each $R^3$ is independently carboxyl, carboxyalkyl (2-6C) or a salt, amide, ester or acyl hydrazone thereof, or is alkyl (1-6C);
$R^4$ is CH=CH$_2$ or —CH(OR$^{4'}$)CH$_3$ wherein $R^{4'}$ is H, or alkyl (1-6C) optionally substituted with a hydrophilic substituent.

21. The method of claim 20 wherein said green porphyrin is of the formula

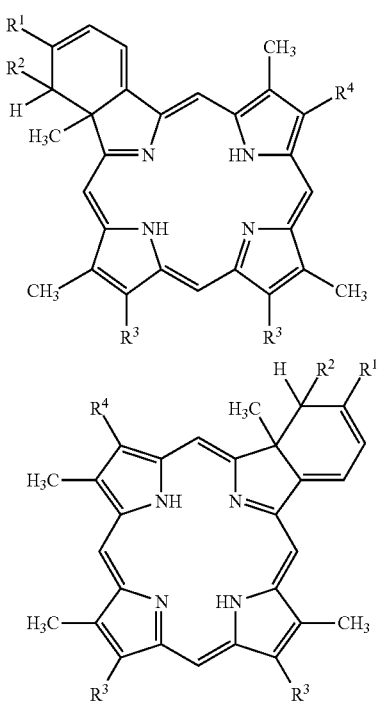

wherein each of $R^1$ and $R^2$ is independently carbalkoxyl (2-6C);

one $R^3$ is carboxyalkyl (2-6C) and the other $R^3$ is the ester of a carboxyalkyl (2-6C) substituent; and
$R^4$ is CH=CH$_2$ or —CH(OH)CH$_3$.

22. The method of claim 21 wherein said green porphyrin is of the formula

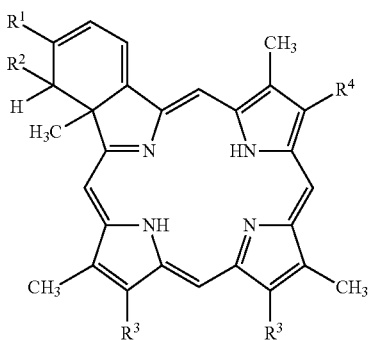

and
wherein $R^1$ and $R^2$ are methoxycarbonyl;
one $R^3$ is —CH$_2$CH$_2$COOCH$_3$ and the other $R^3$ is CH$_2$CH$_2$COOH; and
$R^4$ is CH=CH$_2$.

23. The method of claim 11 wherein said photoactive compound is contained in a liposomal preparation.

24. The method of claim 11, wherein the light is emitted from a laser.

* * * * *